United States Patent
Thomas et al.

(10) Patent No.: US 10,932,789 B2
(45) Date of Patent: Mar. 2, 2021

(54) LIGATION CLIP WITH LATCHING AND RETENTION FEATURES

(71) Applicant: Covidien LP, Mansfield, MA (US)

(72) Inventors: Justin Thomas, New Haven, CT (US); Eric Brown, Haddam, CT (US); Gregory R. Morck, Middletown, CT (US); Roy J. Pilletere, North Haven, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 116 days.

(21) Appl. No.: 16/261,649

(22) Filed: Jan. 30, 2019

(65) Prior Publication Data

US 2019/0314031 A1 Oct. 17, 2019

Related U.S. Application Data

(60) Provisional application No. 62/655,854, filed on Apr. 11, 2018.

(51) Int. Cl.
*A61B 17/122* (2006.01)

(52) U.S. Cl.
CPC ................. *A61B 17/1227* (2013.01)

(58) Field of Classification Search
CPC .............. A61B 17/128; A61B 17/1285; A61B 17/1225; A61B 17/1222; A61B 17/122; A61B 17/1227; A61B 2017/1125; A61M 39/284; A61M 39/286
See application file for complete search history.

(56) References Cited

U.S. PATENT DOCUMENTS

| | | | |
|---|---|---|---|
| 3,439,523 A | 4/1969 | Wood | |
| 3,713,533 A | 1/1973 | Reimels | |
| 4,076,120 A | 2/1978 | Carroll et al. | |
| 4,146,130 A | 3/1979 | Samuels et al. | |
| 4,187,712 A | 2/1980 | Samuels et al. | |
| 4,212,303 A | 7/1980 | Nolan | |
| 4,212,390 A | 7/1980 | Raczkowski et al. | |
| 4,294,355 A | 10/1981 | Jewusiak et al. | |

(Continued)

FOREIGN PATENT DOCUMENTS

| | | |
|---|---|---|
| BE | 654195 A | 2/1965 |
| CN | 204839635 U | 12/2015 |

(Continued)

OTHER PUBLICATIONS

European Search Report dated Sep. 2, 2019, issued in EP Appln. No. 19168517.

*Primary Examiner* — George J Ulsh
*Assistant Examiner* — Andrew P. Restaino
(74) *Attorney, Agent, or Firm* — Carter, DeLuca & Farrell LLP

(57) ABSTRACT

A surgical ligation clip includes a first jaw, a second jaw, and a hinge portion that pivotably couples the first jaw to the second jaw. The first and second jaws define respective clamping surfaces and include spaced bosses. Each of the spaced bosses include a transverse portion and a head portion that is oversized and has a diameter that is larger than the diameter of the transverse portions. The oversized head portions allow for the ligation clips to be securely supported on a clip applicator.

20 Claims, 7 Drawing Sheets

(56) References Cited

U.S. PATENT DOCUMENTS

| | | |
|---|---|---|
| 4,344,531 A | 8/1982 | Giersch |
| 4,346,869 A | 8/1982 | MacNeill |
| 4,361,229 A | 11/1982 | Mericle |
| 4,390,019 A | 6/1983 | LeVeen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |
| 4,487,205 A | 12/1984 | Di Giovanni et al. |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,423,831 A | 6/1995 | Nates |
| 5,564,262 A | 10/1996 | Bevis et al. |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 | 4/2001 | Levinson |
| 6,228,097 B1 | 5/2001 | Levinson et al. |
| 6,273,253 B1 | 8/2001 | Forster et al. |
| 6,306,150 B1 | 10/2001 | Levinson |
| 6,391,035 B1 | 5/2002 | Appleby et al. |
| 6,419,682 B1 | 7/2002 | Appleby et al. |
| 6,421,920 B1 | 7/2002 | Jensen |
| 6,460,700 B2 | 10/2002 | Weisshaupt |
| 6,460,749 B1 | 10/2002 | Levinson et al. |
| 6,780,195 B2 | 8/2004 | Porat |
| 6,824,547 B2 | 11/2004 | Wilson, Jr. et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Iaconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 2002/0046961 A1 | 4/2002 | Levinson et al. |
| 2002/0177863 A1 | 11/2002 | Mandel et al. |
| 2004/0199178 A1 | 10/2004 | Small |
| 2005/0165423 A1 | 7/2005 | Gallagher et al. |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2009/0088783 A1 | 4/2009 | Kennedy et al. |
| 2009/0171380 A1* | 7/2009 | Whiting ............... A61B 17/122 606/158 |
| 2011/0224700 A1 | 9/2011 | Schmidt et al. |
| 2011/0295291 A1 | 12/2011 | Trivisani |
| 2012/0083803 A1 | 4/2012 | Patel et al. |
| 2012/0226291 A1 | 9/2012 | Malizia et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2014/0054192 A1 | 2/2014 | Chancibot |
| 2014/0236170 A1* | 8/2014 | Kethman ........... A61B 17/1227 606/120 |
| 2014/0243862 A1 | 8/2014 | Bagaoisan et al. |
| 2014/0276970 A1 | 9/2014 | Messerly et al. |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0185029 A1 | 7/2018 | Lebens, III |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |

FOREIGN PATENT DOCUMENTS

| | | |
|---|---|---|
| CN | 106264647 A | 1/2017 |
| DE | 10116168 A1 | 11/2001 |
| GB | 253710 A | 3/2001 |

* cited by examiner

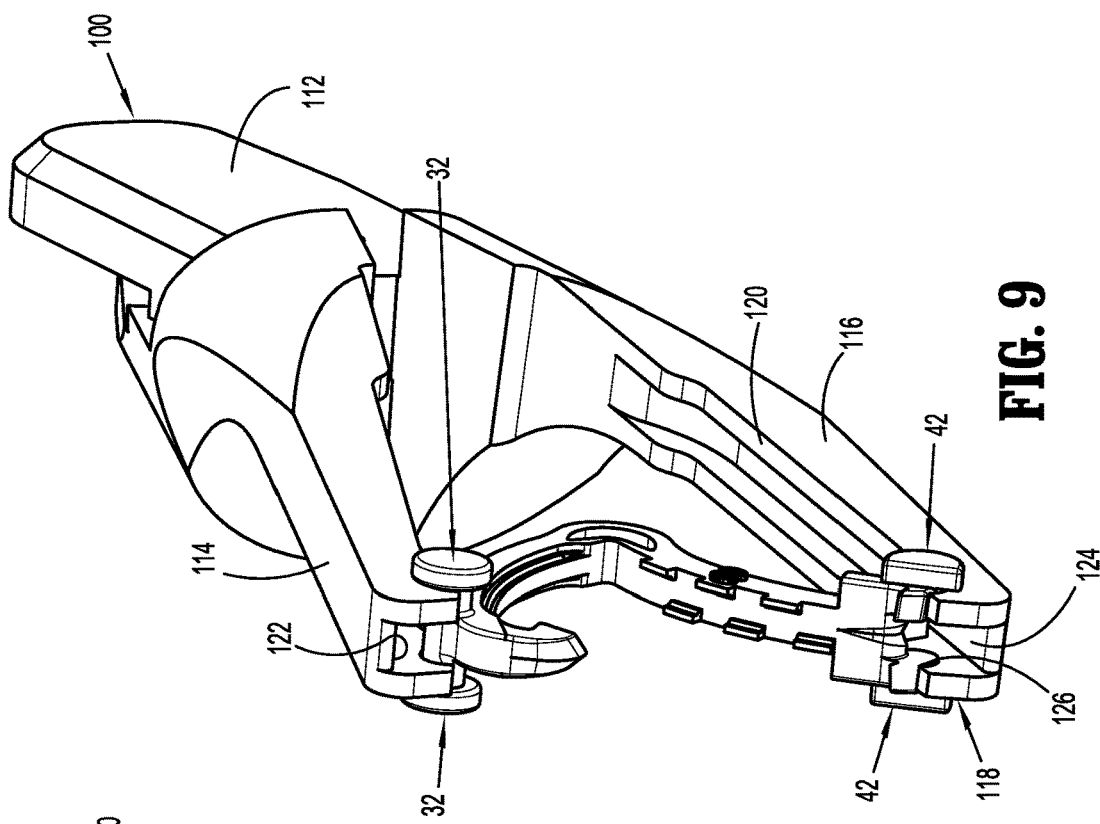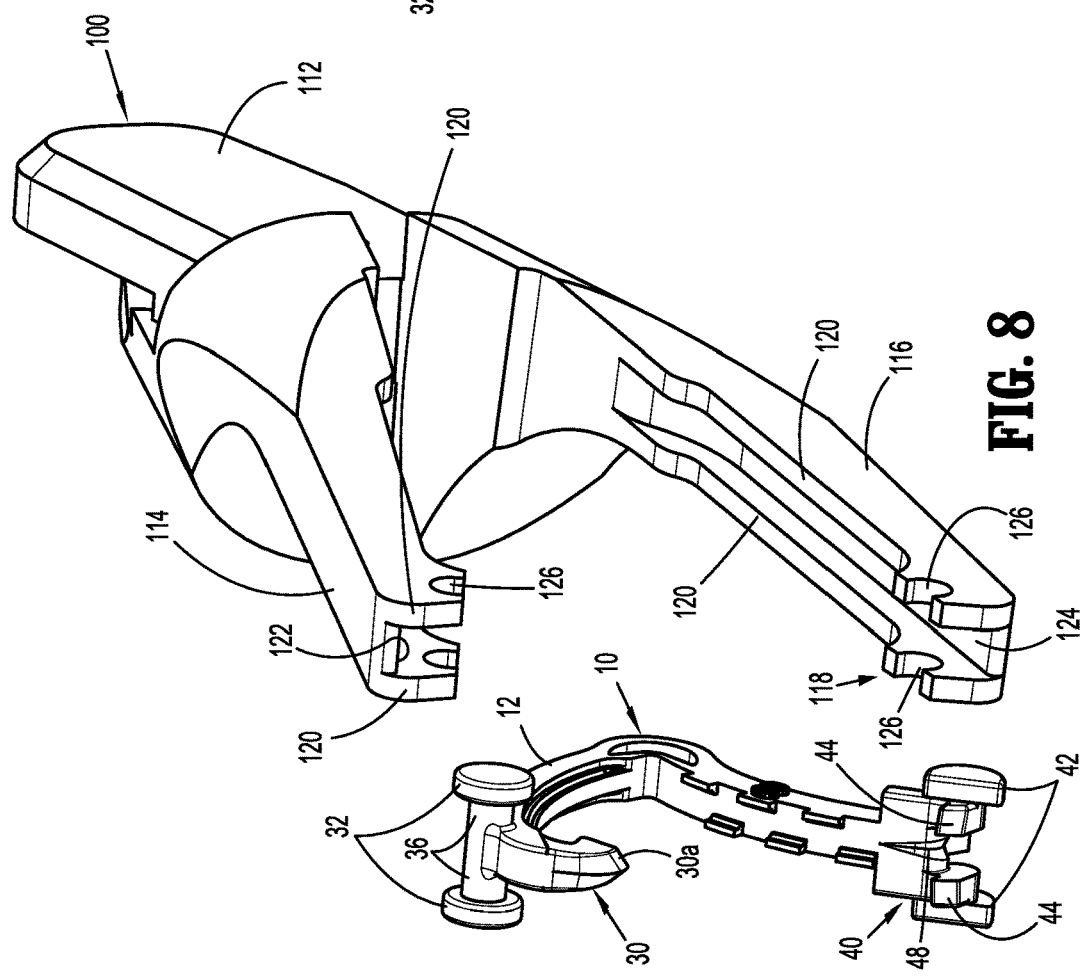

LIGATION CLIP WITH LATCHING AND RETENTION FEATURES

CROSS-REFERENCE TO RELATED APPLICATION

This application claims the benefit of and priority to U.S. Provisional Patent Application No. 62/655,854 filed Apr. 11, 2018, the entire disclosure of which is incorporated by reference herein.

BACKGROUND

1. Technical Description

The present disclosure is directed to ligation clips for sealing body vessels and, more particularly, to ligation clips that include applicator engagement structure to more securely support the ligation clips on a surgical clip applicator.

2. Background of Related Art

Ligation clips are well known in the surgical arts and are commonly used during a variety of surgical procedures to ligate tissue, e.g., a body vessel. Ligation clips include first and second jaws that are pivotably coupled to each other such that the ligation clip is movable between an open position and a clamped position. Typically, each of the first and second jaws includes bosses that are configured to engage jaws of a clip applicator to support the ligation clip on the clip applicator. The jaws of the clip applicator include recesses that receive the bosses to support the ligation clip on the clip applicator to facilitate placement of the ligation clip about body tissue. The jaws of the clip applicator are movable between open and clamped positions to move the ligation clip between the open and clamped positions.

In current clip designs, the bosses on the first and second jaws of the ligation clips and the recesses on the jaws of the clip applicator are not configured to securely fasten the ligation clip on the clip applicator. Thus, it is not unusual for the ligation clip to become dislodged from the clip applicator and fall into a body cavity as the clip applicator is maneuvered around tissue during placement of the ligation clip. When a ligation clip becomes dislodged from the clip applicator, the clinician must remove the clip applicator from the body cavity, retrieve the ligation clip from the body cavity, and place a new ligation clip onto the jaws of the clip applicator. This process is time consuming and wasteful.

A continuing need exists in the art for a ligation clip with improved engagement structure to more effectively secure the ligation clip to a clip applicator.

SUMMARY

One aspect of the disclosure is directed to a ligation clip including a first jaw, and a second jaw. The first jaw includes a body defining a first clamping surface and supporting a first pair of spaced bosses. The second jaw includes a body defining a second clamping surface. The second jaw is coupled to the first jaw such that the ligation clip is movable between an open position and a clamped position. The second jaw supports a second pair of spaced bosses. Each of the bosses of the first and second pairs of bosses includes a transverse portion and a head portion. The transverse portion extends outwardly of the body of the respective first or second jaw. The head portion is supported on the transverse portion outwardly of the body of the respective first or second jaw. The diameter of the head portion is greater than the diameter of the transverse portion to define a shoulder between the transverse portion and the head portion.

In embodiments, the transverse portions of each of the bosses of the first and second pairs of spaced bosses are cylindrical.

In some embodiments, the transverse portions of each of the bosses of the first and second pairs of spaced bosses are formed by a single member that extends between the head portions of the first and second pairs of spaced bosses.

In certain embodiments, the first jaw includes a longitudinal rib having a tissue engaging surface that is positioned in opposition to the second clamping surface of the second jaw when the ligation clip is in the clamped position.

In embodiments, the second jaw has a first row of protrusions supported on one side of the second clamping surface and a second row of protrusions supported on an opposite side of the second clamping surface.

In some embodiments, each of the protrusions of the first and second rows of protrusions has an inner side wall in opposition to the longitudinal rib when the ligation clip is in the clamped position.

In certain embodiments, the first row of protrusions is laterally spaced from the second row of protrusions to define a channel that extends longitudinally between the first and second rows of protrusions, wherein the channel is positioned to receive the stepped longitudinal rib when the ligation clip is in the clamped position.

In embodiments, the protrusions in the first row of protrusions are longitudinally aligned and spaced from each other and the protrusions in the second row of protrusions are longitudinally aligned and spaced from each other.

In some embodiments, each of the protrusions in the first row of protrusions are longitudinally offset from each of the protrusions in the second row of protrusions such that the protrusions are alternatingly positioned on opposite sides of the second clamping surface along the length of the second clamping surface.

In certain embodiments, the first jaw includes a first locking element and the second jaw includes a second locking element, wherein the first locking element is movable into engagement with the second locking element to retain the ligation clip in the clamped position.

In embodiments, the ligation clip is formed of a polymeric material.

In some embodiments, the second jaw includes a distal portion including spaced teeth that are configured to penetrate tissue.

In certain embodiments, the first locking element includes a hooked portion that extends downwardly and proximally from the first tissue clamping surface and the second locking element defines an engagement surface for receiving the hooked portion.

In embodiments, the second locking element defines a cam surface that engages the hooked portion to bias the hooked portion outwardly of the second locking element such that the hooked portion resiliently returns to an unbiased state after passing over the second locking element to position the hooked portion in contact with the engagement surface.

In some embodiments, the second jaw includes a spring arm that is positioned to engage and be deflected by the first locking element as the ligation clip is moved from the open position to the clamped position, wherein the spring arm is positioned to urge the first and second locking elements to a latched position.

BRIEF DESCRIPTION OF THE DRAWINGS

Various exemplary embodiments of the presently disclosed ligation clip are described herein below with reference to the drawings, wherein:

FIG. 8 is a perspective view from a distal end of the ligation clip shown in FIG. 1 and a clip applicator prior to engagement of the ligation clip to the jaws of the clip applicator; and FIG. 9 is a perspective view from the distal end of the ligation clip and clip applicator shown in FIG. 8 with the ligation clip engaged with the jaws of the clip applicator.

DETAILED DESCRIPTION OF EMBODIMENTS

Figure 1:
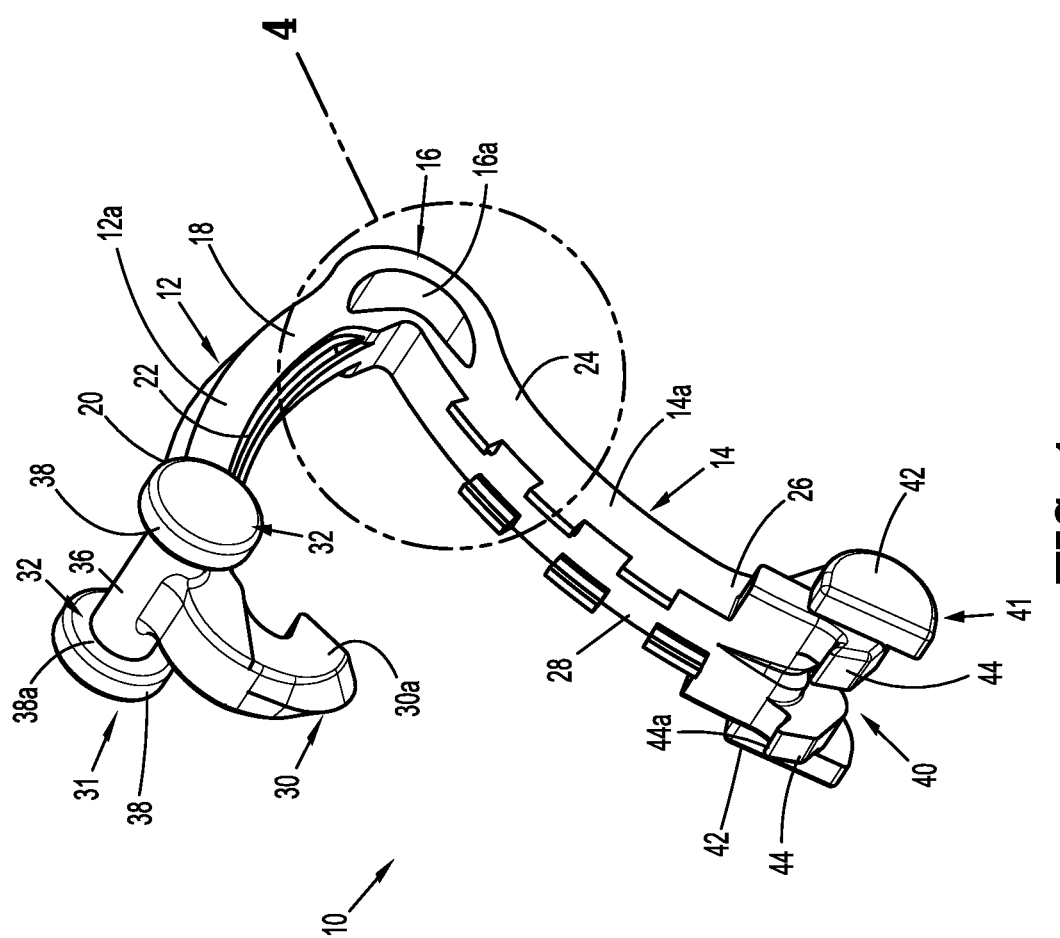
FIG. 1 is a side perspective view of an exemplary embodiment of the presently disclosed ligation clip in an open position.

The presently disclosed ligation clip will now be described in detail with reference to the drawings in which like reference numerals designate identical or corresponding elements in each of the several views. It is to be understood that the disclosed embodiments are merely exemplary of the disclosure and may be embodied in various forms. Well-known functions or constructions are not described in detail to avoid obscuring the present disclosure in unnecessary detail. Specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
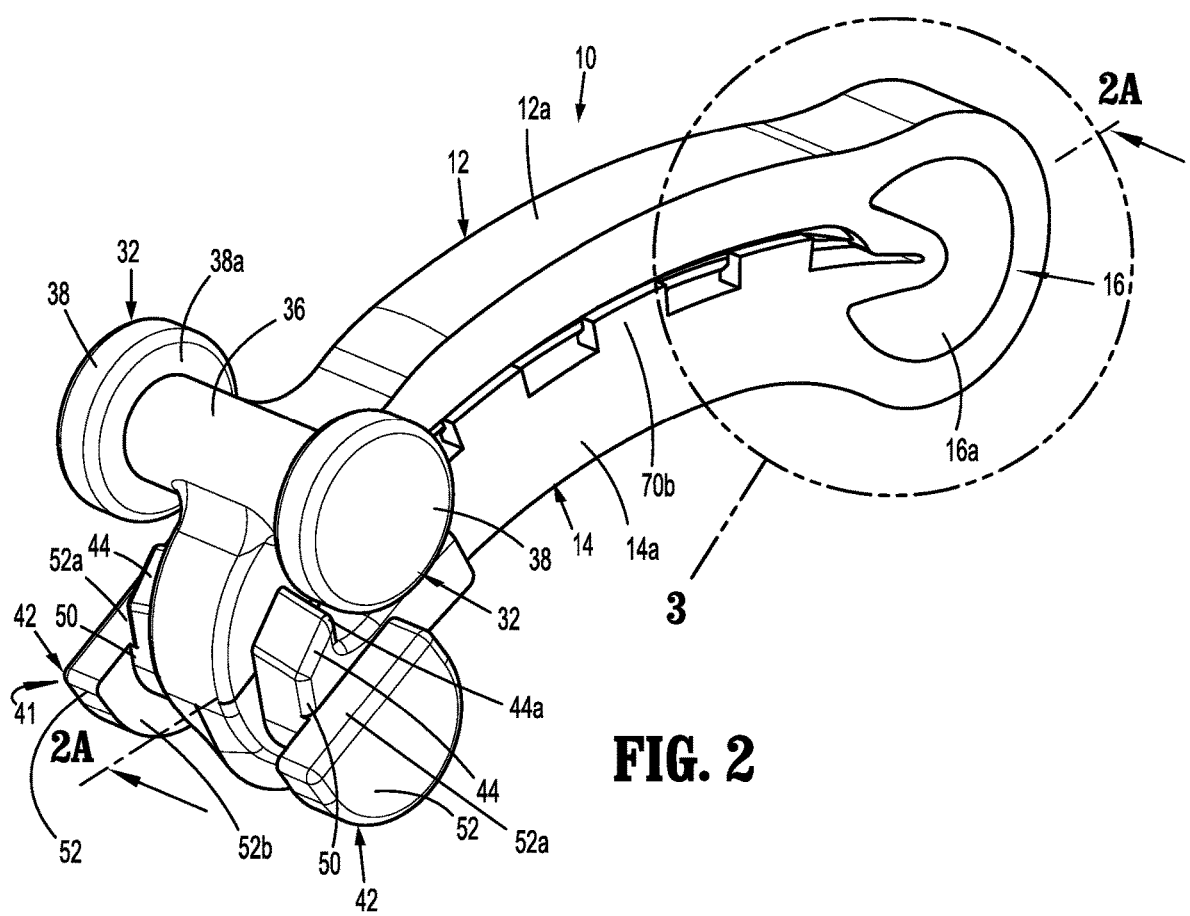
FIG. 2 is a side perspective view of the ligation clip shown in FIG. 1 in the clamped position.
Figure 2A:
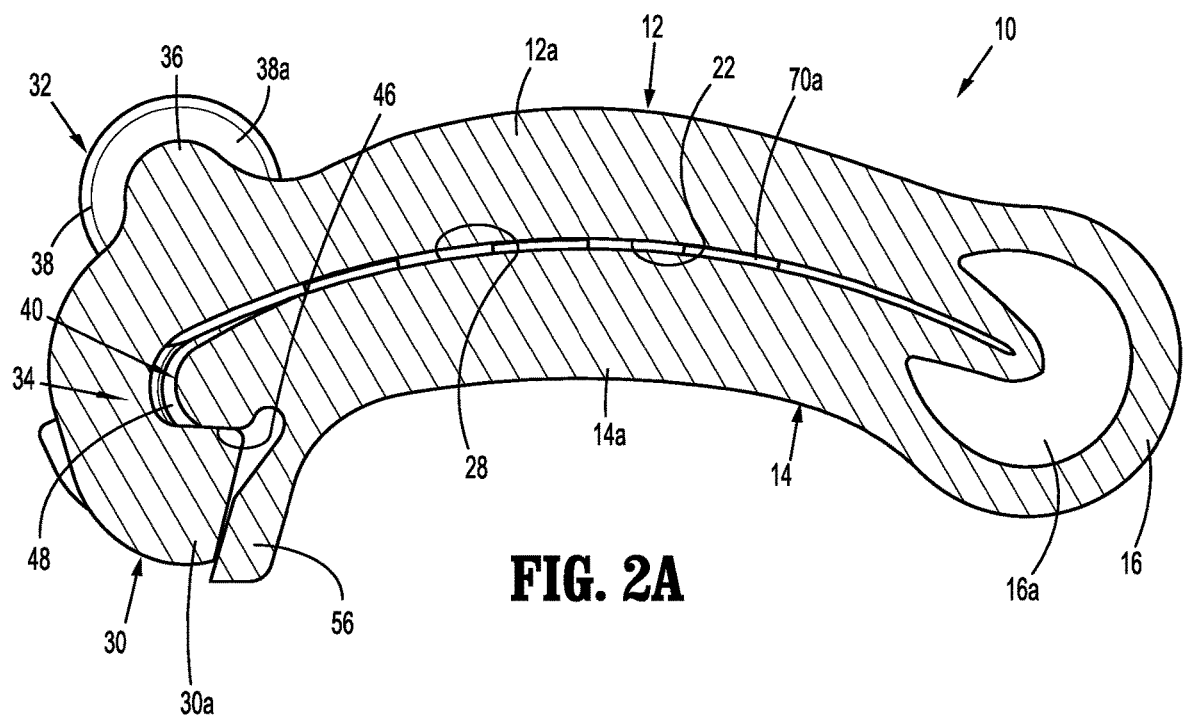
FIG. 2A is a cross-sectional view taken along section line 2A-2A of FIG. 2.
Figure 2B:
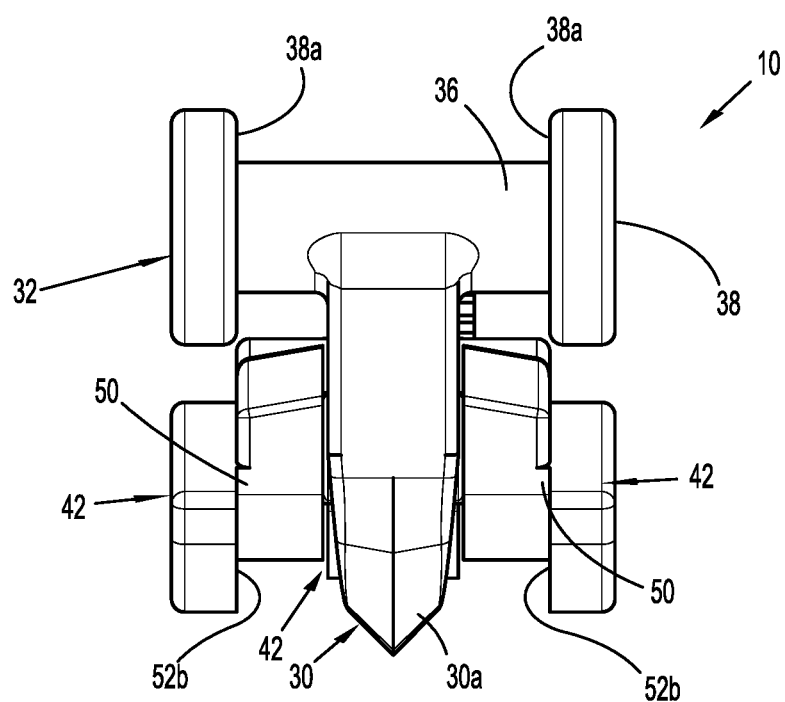
FIG. 2B is a front view of the ligation clip shown in FIG. 2
Figure 3:
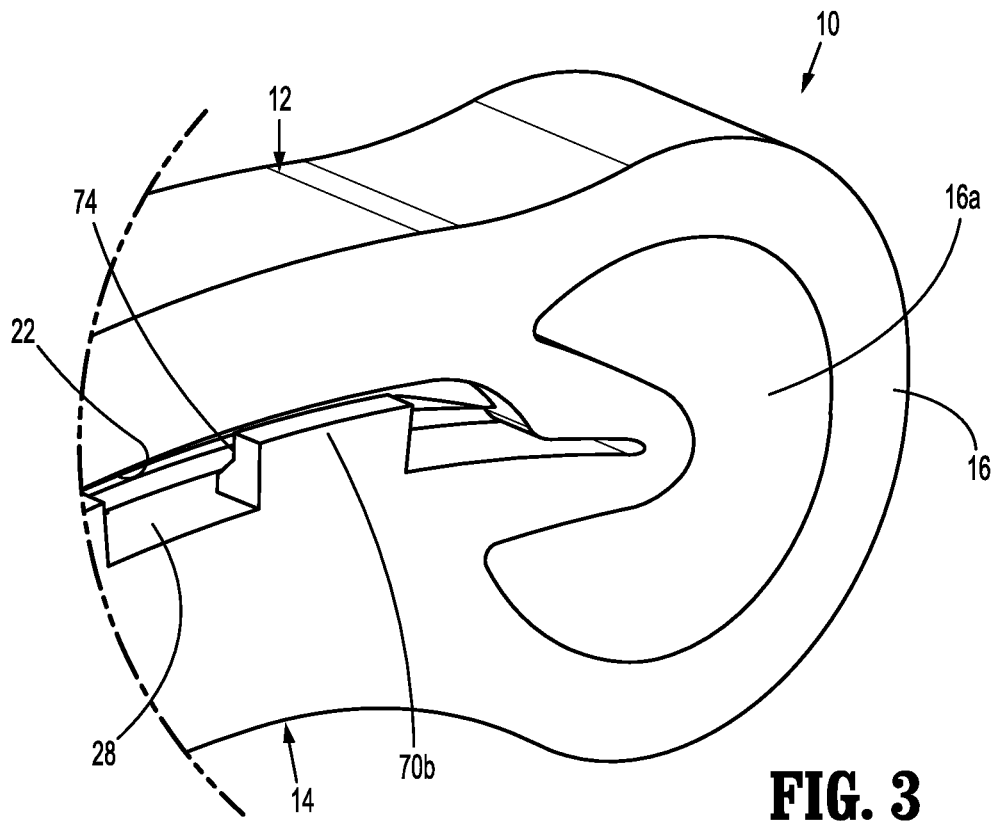
FIG. 3 is an enlarged view of the indicated area of detail shown in FIG. 2.

Referring to FIGS. 1-3, an exemplary embodiment of the presently disclosed ligation clip is shown generally as ligation clip 10. The ligation clip 10 defines a longitudinal axis "Z" (FIG. 2A) and includes a first jaw 12, a second jaw 14, and a hinge portion 16 coupling the first jaw 12 to the second jaw 14. The first jaw 12 is pivotable in relation to the second jaw 14 about the hinge portion 16 to move the ligation clip 10 between an open position (FIG. 1) and a clamped position (FIG. 3). In embodiments, the first and second jaws 12, 14 are curved along the longitudinal axis "Z" (FIG. 6) although other jaw configurations are envisioned. In embodiments, the hinge portion 16 may be integrally formed with the first and second jaws 12, 14, e.g., a living hinge, and may define a crescent shaped through bore 16a to facilitate movement of the first jaw 12 in relation to the second jaw 14 between the open and clamped positions. The through bore 16a also allows for substantially complete closure of the proximal portions of the first and second jaws 12, 14.

The first jaw 12 has a body 12a having a proximal portion 18, a distal portion 20, and a clamping surface 22. The second jaw 14 has a body 14a having a proximal portion 24, a distal portion 26, and a clamping surface 28. The proximal portions 18, 24 of the first and second jaws 12, 14, respectively, are coupled to the hinge portion 16 such that the ligation clip 10 is pivotable between an open position (FIG. 1) and a clamped position (FIG. 2). The distal portion 20 of the first jaw 12 includes a first locking element 30 and engagement structure 31 including spaced bosses 32. The first locking element 30 includes a hooked portion 30a that extends downwardly and proximally from the tissue clamping surface 22 to define a portion of a latching mechanism 34 (FIG. 2A) that is configured to retain the ligation clip 10 in a clamped position as described in further detail below.

The engagement structure 31 of the first jaw 12 including the bosses 32 are supported on the distal portion of the body 12a of the first jaw 12. Each of the bosses 32 includes a transverse portion 36 that extends outwardly of the body 12a of the first jaw 12 and a head portion 38 that is supported on the transverse portion 38 outwardly of the body 12a of the first jaw 12. The head portion 38 has a diameter or width, collectively referred to herein as "diameter", that is greater than the diameter of the transverse portion 36 to define a shoulder 38a between the transverse portion 36 and the head portion 38. In embodiments, the transverse portion 36 and/or the head portion 38 of the bosses 32 is cylindrical although other configurations are envisioned. The transverse portion 36 of the bosses 32 may form part of a single member supported on the distal portion of the first jaw 12 that extends between the head portions 38 of the spaced bosses 32. The head portions 38 of the bosses 32 are positioned outwardly from the body 12a of the first jaw 12 such that the transverse portion 36 are accessible to jaws 114, 116 of a clip applicator 100 (FIG. 8) as described in further detail below to facilitate placement of the ligation clip 10 on the clip applicator 100.

The distal portion 26 of the second jaw 14 includes a second locking element 40, engagement structure 41 including spaced bosses 42, and spaced teeth 44. The spaced teeth 44 are configured to engage and/or penetrate tissue. In embodiments, the teeth 44 have an apex or pointed end 44a that grips and stretches tissue as the ligation clip 10 is moved from the open position (FIG. 1) towards the clamped position (FIG. 2) to improve the ligating characteristics of the ligation clip 10. The second locking element 40 defines an engagement surface 46 (FIG. 2A) and a cam surface 48. The cam surface 48 and the engagement surface 46 are configured to receive and guide the first locking element 30 into locking engagement with the second locking element 40 when the ligation clip 10 is moved to the clamped position (FIG. 3) to secure the ligation clip 10 in the clamped position. In particular, the cam surface 48 is configured to deflect the first locking element 30 outwardly in a distal direction as the first locking element 30 passes over the cam surface 48 such that when the first locking element 30 moves past the cam surface 48, the first locking element 30 resiliently moves into engagement with the second locking element 40 (FIG. 2A).

The bosses 42 of the engagement structure 41 (FIG. 2) of the second jaw 14 are similar to the bosses 32 of the first jaw 12. More specifically, the bosses 42 each include a transverse portion 50 and a head portion 52. In embodiments, the head portion has a flat surface 52a that faces the spaced bosses 42. The head portion 52 has a diameter that is greater than the diameter of the transverse portion 50 to define a shoulder 52b between the transverse portion 50 and the head portion 52. In embodiments, the transverse portion 50 and/or the head portion 52 of the bosses 42 is cylindrical although other configurations are envisioned, e.g., square, triangular, etc. The transverse portion 50 of each of the bosses 52 may form part of a single member supported on the distal portion of the second jaw 14 that extends between the spaced bosses 42. The head portions 50 of the bosses 42 are positioned outwardly from the body 14a of the second jaw 14 such that the transverse portions 50 of the bosses 42 are accessible to the jaws 114, 116 of the clip applicator 100 (FIG. 8) to facilitate placement of the ligation clip 10 on the clip applicator 100 as described in further detail below.

The second jaw 14 includes a spring arm 56 that is positioned to engage the first locking element 30 when the ligation element 10 is moved to the clamped position to retain the first locking element 30 and the second element 40 in the latched position (FIG. 2A). The spring arm 56 is positioned to engage and be deflected by the first locking element 30 to create a compressive force within the spring arm 56 that presses against the second locking element.

The first clamping surface 22 is substantially flat and supports a longitudinal rib 60 (FIG. 4) including a tissue engaging surface 62 that is in opposition with the clamping surface 28 of the second jaw 14 when the ligation clip 10 is in the clamped position (FIG. 3). In embodiments, the longitudinal rib 60 is rectangular although other rib configurations are envisioned. In some embodiments, the tissue engaging surface 62 of the longitudinal rib 60 is substantially flat and extends substantially the entire length of the tissue clamping surface 22. Alternately, it is envisioned that the longitudinal rib 60 may include one or more longitudinal rib sections that are longitudinally spaced from each other and extend over a length less than the entire length of the tissue clamping surface 22, e.g., 50-80 percent of the length of the tissue clamping surface 22.

Figure 4:
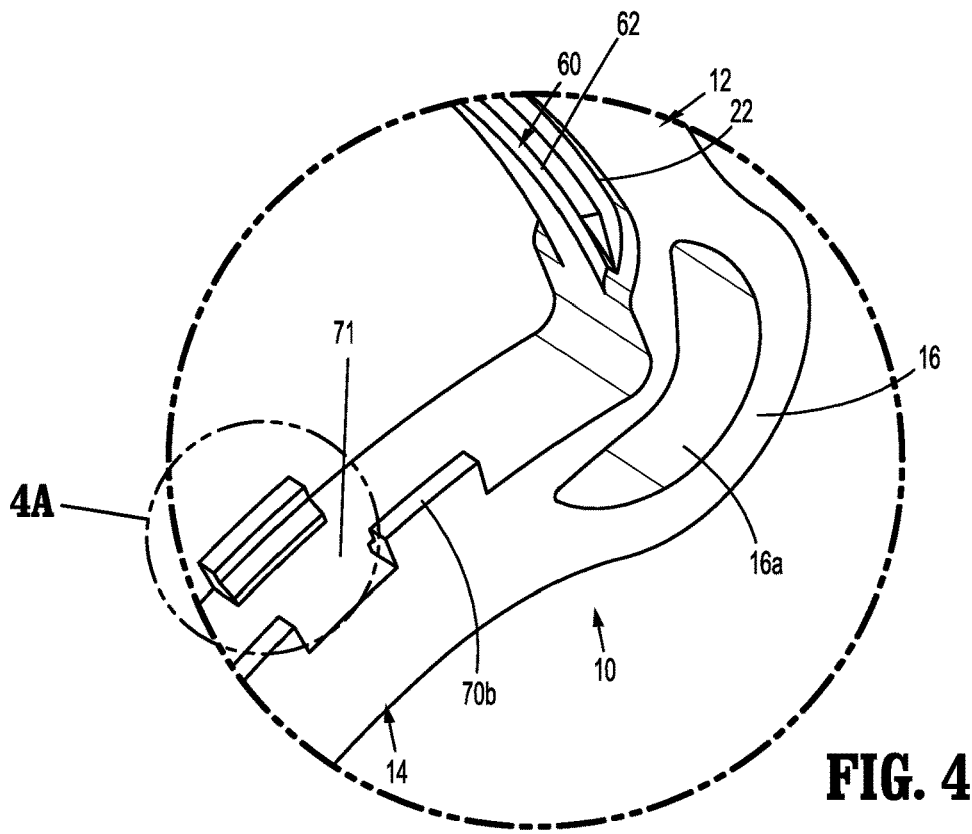
FIG. 4 is an enlarged view of the indicated area of detail shown in FIG. 1.
Figure 4A:
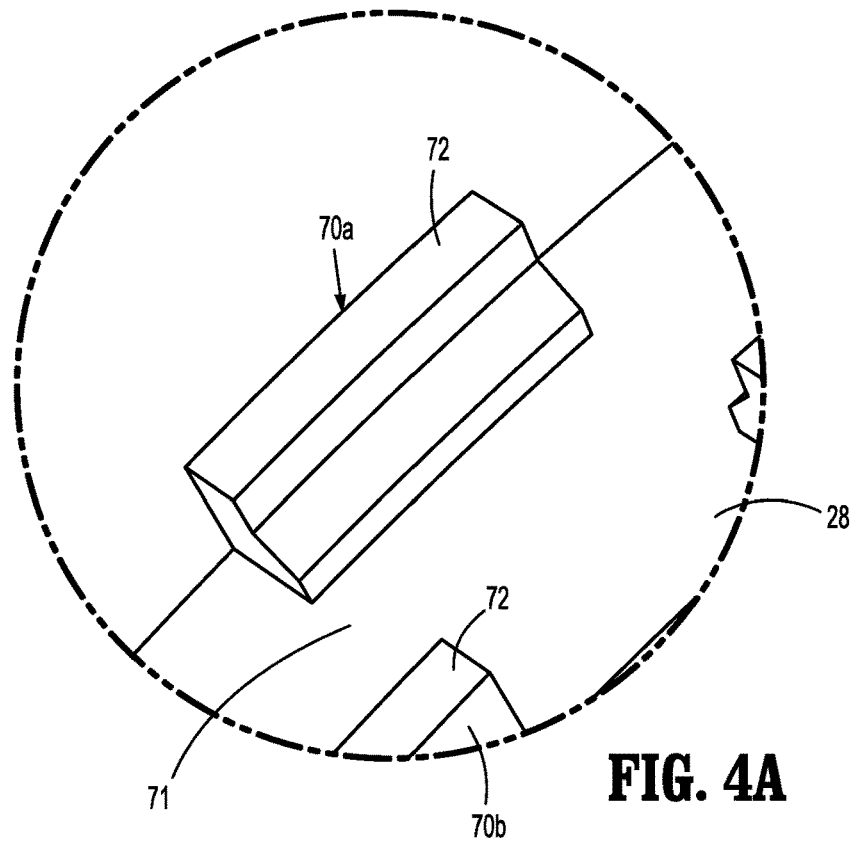
FIG. 4A is an enlarged view of the indicated area of detail shown in FIG. 4.

Referring also to FIGS. 4 and 4A, the second clamping surface 28 is substantially flat and supports a first row of protrusions 70a and a second row of protrusions 70b. Each of the protrusions 70a of the first row of protrusions 70a is spaced from but longitudinally aligned with each of the other protrusions 70a in the first row along a first side of the second clamping surface 28. Similarly, each of the protrusions 70b of the second row of protrusions 70b is longitudinally aligned with each of the other protrusions 70b in the second row along a second side of the second clamping surface 28 opposite to the first side. The protrusions 70a, 70b may have a width that is less than half the width of the clamping surface 28 to define an unobstructed central channel 71 between the first and second rows of protrusions 70a, 70b on the second clamping surface 28. The central channel 71 is receives the longitudinal rib 60 when the ligation clip 10 is in the clamped position. In embodiments, each of the protrusions 70a on the first side of the clamping surface 28 is longitudinally offset from each of protrusions 70b positioned on the other side of the clamping surface 28 such that the protrusions 70a and 70b are alternatingly positioned on opposite sides of the clamping surface 28 along the length of the clamping surface 28.

Each of the protrusions 70a, 70b includes a tissue engaging surface 72 (FIG. 4A) and an inner side wall 74. The tissue engaging surface 72 is positioned in opposition to the clamping surface 22 of the first jaw 12 when the ligation clip 10 is in the clamped position. The inner side wall 74 of each of the protrusions 70a, 70b is positioned in opposition to the longitudinal rib 60 when the ligation clip 10 is in the clamped position (FIG. 2A).

In embodiments, the surgical ligation clip 10 may be made, in whole or in part, of a resilient bioabsorbable and/or biocompatible polymeric material. Examples of suitable bioabsorbable and/or biocompatible polymers include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The clip may also be made of a polymer material or materials in combination with radiolucent metal alloys. Alternately, other materials may be used to form the clip 10 including biocompatible metals, plastics and composites.

Figure 5:
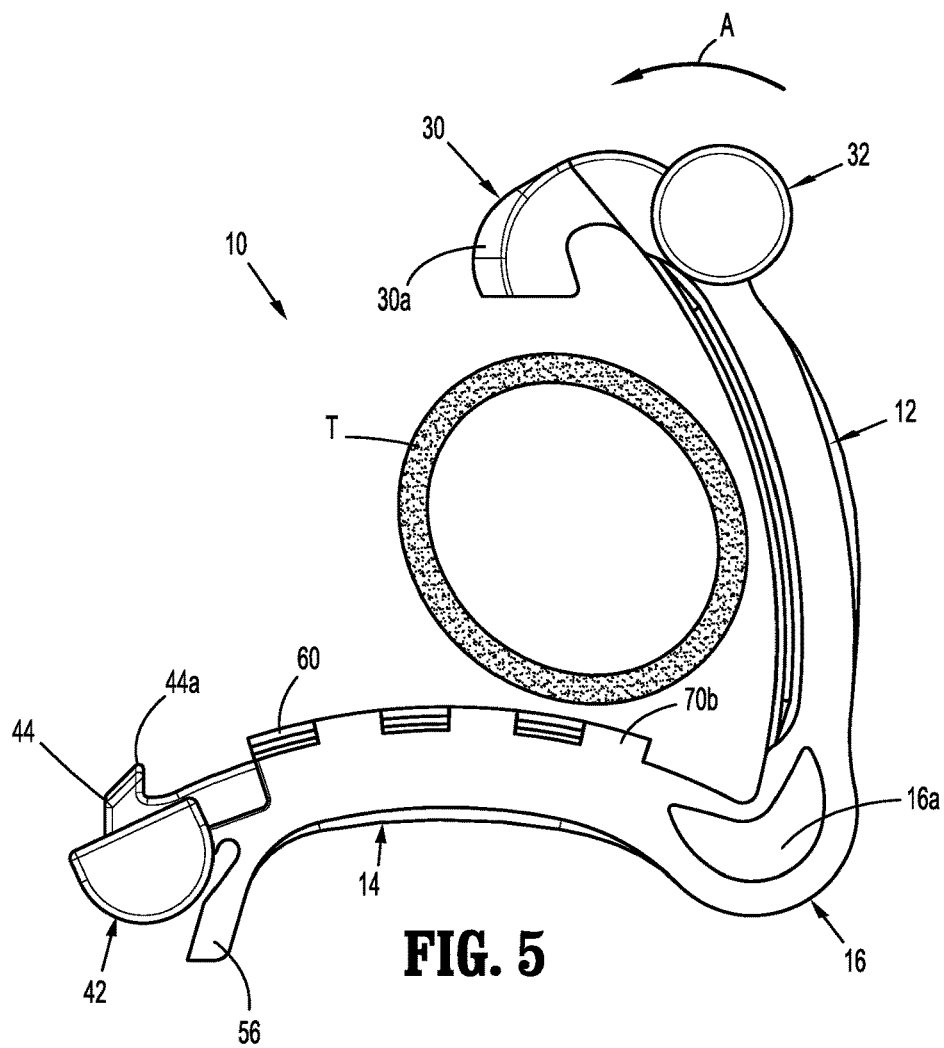
FIG. 5 is a side view of the ligation clip shown in FIG. 1 in the open position placed about tissue.
Figure 6:
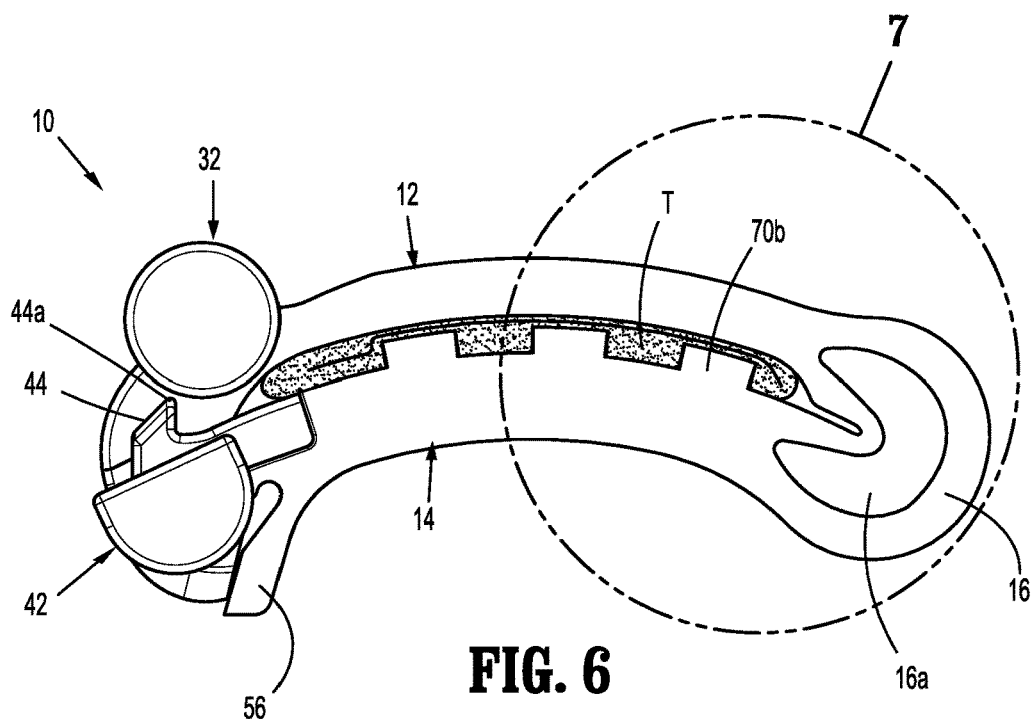
FIG. 6 is a side view of the ligation clip shown in FIG. 5 in the clamped position placed about tissue.
Figure 7:
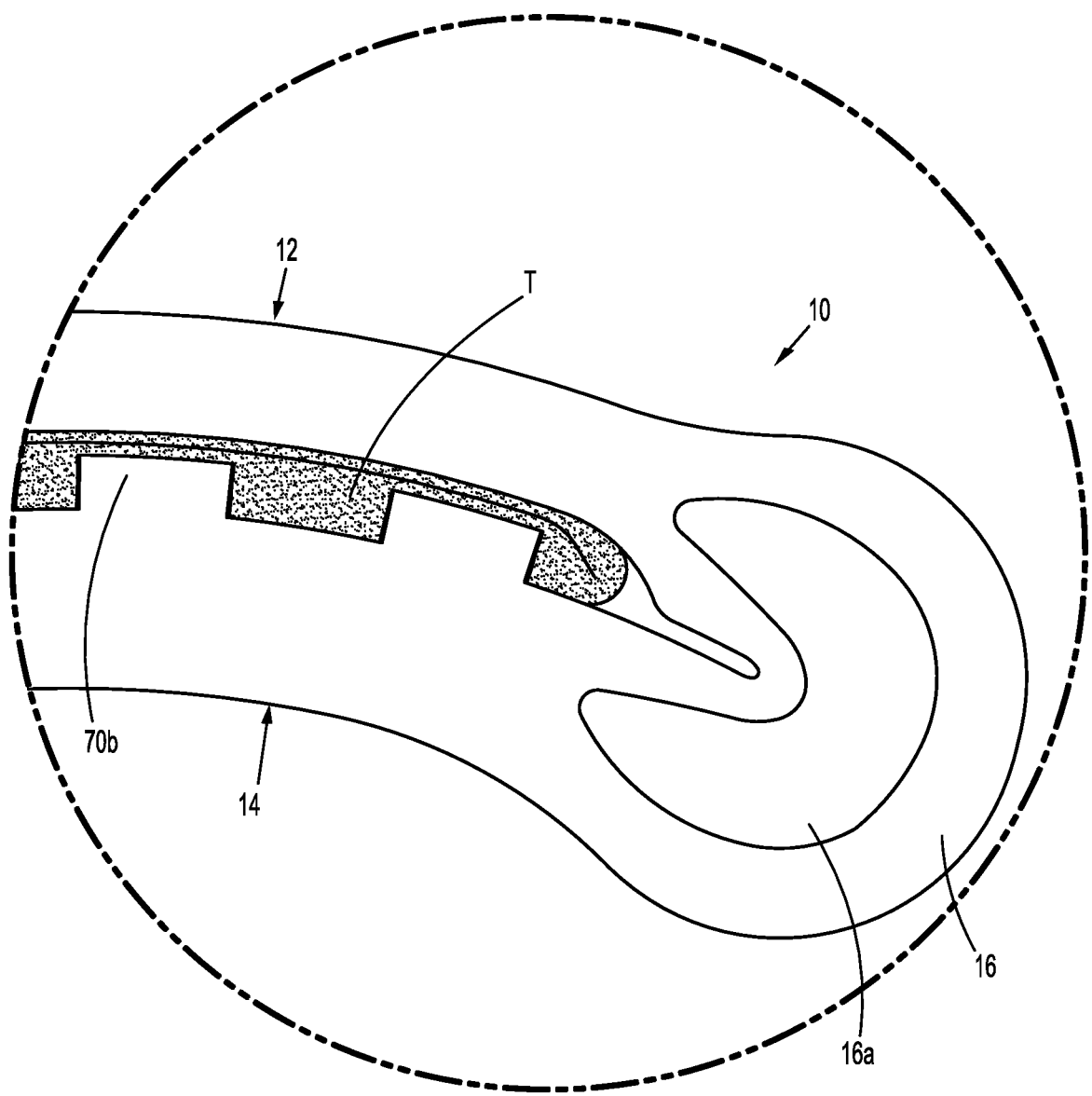
FIG. 7 is an enlarged view of the indicated area of detail shown in FIG. 6.

Referring to FIGS. 5-7, in use, the ligation clip 10 is placed about tissue "T", e.g., a body vessel, such that the tissue "T" is positioned between the tissue clamping surface 22 of the first jaw 12 and the tissue clamping surface 28 of the second jaw 14. When the ligation clip 10 is moved from the open position (FIG. 5) to the closed position (FIG. 6) in the direction indicated by arrow "A" in FIG. 5, the first jaw 12 pivots in relation to the second jaw 14 about the hinge portion 16 to move the hooked portion 30a of the first locking element 30 into engagement with the portion of the second jaw 14 defining the engagement surface 46 to secure the ligation clip 10 in the clamped position. In the clamped position, the tissue "T" is compressed between the first and second clamping surfaces 22, 28 of the first and second jaws 12, 14, and between the longitudinal rib 60 of the first jaw 12 and the protrusions 70a, 70b of the second jaw 14.

The above described ligation clip 10 including a first jaw 12 having a longitudinal rib 60 and a second jaw 14 including first and second rows of protrusions 70a, 70b that are in opposition to the longitudinal rib in the clamped position of the ligation clip 10 improve the retention forces of the ligation clip 10 on the tissue "T" and minimize the likelihood that the ligation clip 10 will slide in a direction parallel to the clamping surfaces 22, 28 of the first and second jaws 12, 14, respectively, after the ligation clip 10 has been clamped about the tissue "T".

Referring to FIGS. 8 and 9, the bosses 32, 42 of the first and second jaws 12, 14, respectively, are configured to securely support the ligation clip 10 on the clip applicator 100. In embodiments, the clip applicator 100 includes body 112, a first jaw 114, and a second jaw 116. The first and second jaws 114, 116 are pivotably supported on a distal end of the body 112 and are movable between open and closed positions. Each of the first and second jaws 114, 116 of the clip applicator 100 includes a coupling structure 116 configured to engage the bosses 32, 42 of the first and second jaws 12, 14 of the ligation clip 10 to securely support the ligation clip 10 on the jaws 114, 116 of the clip applicator 100.

Each of the coupling structures 118 includes two spaced apart support ribs 120 that extend longitudinally along the first and second jaws 114, 116 of the clip applicator 100. The support ribs 120 of the first jaw 114 define a channel 122 on the first jaw 114 that receives the first jaw 12 of the ligation clip 10 and the support ribs 120 of the second jaw 114 define a channel 124 on the second jaw 114 that receives the second jaw 14 of the ligation clip 10. Each of the support ribs 120 defines a concavity 126 on a distal portion of the rib 120. The concavities 126 defined in the ribs 120 of the first jaw 114 are dimensioned and configured to receive the transverse portions 36 of the bosses 32 of the first jaw 12 of the ligation clip 10 and the concavities 126 defined in the ribs 120 of the second jaw 116 are dimensioned and configured to receive the transverse portions 50 of the bosses 42 of the second jaw 14 of the ligation clip 10. In embodiments, the diameter of the concavities 126 corresponds to the diameter of the transverse portions 36, 50 of the bosses 32, 42 and is smaller than the respective diameter of the head portions 38, 52 of the bosses 32, 42, respectively to prevent passage of the head portions through the concavities 126.

In use, the transverse portions 36 of the bosses 32 of the first jaw 12 of the ligation clip 10 are received within the concavities 126 of the first jaw 114 of the clip applicator 100 and the transverse portions 50 of the bosses 42 of the second jaw 14 of the ligation clip 10 are received within the concavities 126 of the second jaw 116. When the ligation clip 10 is supported on the clip applicator 100, the oversized head portions 38, 52 of the bosses 32, 42 of the first and second jaws 12, 14 of the ligation clip 10 prevents the ligation clip 10 from moving laterally and becoming dislodged from the clip applicator 100. This minimizes the likelihood of a ligation clip 10 from becoming dislodged from a clip applicator 100 while maneuvering of the clip applicator 100 about tissue during placement of the ligation clip 10 on tissue.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A ligation clip comprising:
  a first jaw including a body defining a first clamping surface, the first jaw supporting a first pair of spaced bosses; and
  a second jaw including a body defining a second clamping surface, the second jaw being pivotably coupled to the first jaw such that the ligation clip is movable between an open position and a clamped position, the second jaw supporting a second pair of spaced bosses;
  each of the bosses of the first and second pairs of bosses including a transverse portion and a head portion, the transverse portion fixed to the head portion and extending outwardly of the body of the first or second jaw, and the head portion being supported on the transverse portion outwardly of the body of the first or second jaw, wherein the diameter of the head portion is greater than the diameter of the transverse portion to define a shoulder between the transverse portion and the head portion, the shoulder of each of the bosses of the first and second pairs of bosses facing the body of the first or second jaw.

2. The ligation clip of claim 1, wherein the transverse portions of each of the bosses of the first and second pairs of spaced bosses is cylindrical.

3. The ligation clip of claim 1, wherein the transverse portions each of the bosses of the first pair of spaced bosses are formed by a single member that extends between the head portions.

4. The ligation clip of claim 1, wherein the first jaw includes a longitudinal rib having a tissue engaging surface that is positioned in opposition to the second clamping surface of the second jaw when the ligation clip is in the clamped position.

5. The ligation clip of claim 4, wherein the second jaw has a first row of protrusions supported on one side of the second clamping surface and a second row of protrusions supported on an opposite side of the second clamping surface, each of the protrusions of the first and second rows of protrusions having an inner side wall in opposition to the longitudinal rib when the ligation clip is in the clamped position.

6. The ligation clip of claim 5, wherein the first row of protrusions is laterally spaced from the second row of protrusions to define a channel that extends longitudinally between the first and second rows of protrusions, the channel being positioned to receive the longitudinal rib when the ligation clip is in the clamped position.

7. The ligation clip of claim 6, wherein the protrusions in the first row of protrusions are longitudinally aligned and spaced from each other and the protrusions in the second row of protrusions are longitudinally aligned and spaced from each other.

8. The ligation clip of claim 7, wherein each of the protrusions in the first row of protrusions are longitudinally offset from each of protrusions in the second row of protrusions such that the protrusions are alternatingly positioned on opposite sides of the second clamping surface along the length of the second clamping surface.

9. The ligation clip of claim 1, wherein the first jaw includes a first locking element and the second jaw includes a second locking element, the first locking element being movable into engagement with the second locking element to retain the ligation clip in the clamped position.

10. The ligation clip of claim 9, wherein the first locking element includes a hooked portion that extends downwardly and proximally from the first tissue clamping surface and the second locking element defines an engagement surface for engaging the hooked portion.

11. The ligation clip of claim 10, wherein the second locking element defines a cam surface that engages the hooked portion to bias the hooked portion outwardly of the second locking element such that the hooked portion resiliently returns to an unbiased state after passing over the second locking element to position the hooked portion in contact with the engagement surface.

12. The ligation clip of claim 1, wherein the ligation clip is formed of a polymeric material.

13. The ligation clip of claim 1, wherein the second jaw includes a distal portion, the distal portion including spaced teeth that are configured to penetrate tissue.

14. The ligation clip of claim 13, wherein the teeth have an apex that grips and stretches tissue as the ligation clip is moved to the clamped position.

15. The ligation clip of claim 9, wherein the second jaw includes a spring arm that is positioned to engage and be deflected by the first locking element as the ligation clip is moved from the open position to the clamped position, the spring arm being positioned to urge the first and second locking elements to a latched position.

16. A ligation clip comprising:
  a first jaw including a body defining a first clamping surface, the first jaw supporting spaced bosses; and a second jaw including a body defining a second clamping surface, the second jaw being coupled to the first jaw and movable in relation to the first jaw between open and clamped positions;

each of the spaced bosses including a transverse portion and a head portion, the transverse portion fixed to the head portion and extending outwardly of the body of the first jaw, and the head portion being supported on the transverse portion outwardly of the body of the first jaw, wherein the diameter of the head portion is greater than the diameter of the transverse portion to define a shoulder between the transverse portion and the head portion, the shoulder of each of the spaced bosses facing the body of the first jaw.

17. The ligation clip of claim 16, wherein the transverse portion of each of the spaced bosses is cylindrical.

18. The ligation clip of claim 17, wherein the transverse portions of the spaced bosses are formed by a single member that extends between the heads of the spaced bosses.

19. A ligation clip comprising:
a first jaw including a body defining a first clamping surface, the first jaw supporting spaced bosses; and
a second jaw including a body defining a second clamping surface, the second jaw being coupled to the first jaw and movable in relation to the first jaw between open and clamped positions;
each of the spaced bosses including a head portion spaced outwardly of the body of the first jaw, a transverse portion, the transverse portion fixed to the head portion, each of the head portions defining a shoulder that faces the body of the first jaw, the shoulder of each of the spaced bosses facing the body of the first jaw.

20. The ligation clip of claim 19, further including spaced bosses supported on the second jaw, each of the spaced bosses supported on the second jaw including a head portion spaced outwardly of the body of the second jaw, each of the head portions of the spaced bosses supported on the second jaw defining a shoulder that faces the body of the second jaw.

\* \* \* \* \*